United States Patent [19]

Bernet et al.

[11] 4,105,137

[45] Aug. 8, 1978

[54] PROCESS AND DEVICE FOR THE AUTOMATIC DILUTION OF SOLUTIONS

[75] Inventors: Rudolf Bernet, Zeglingen; Hans Koller; Eugen Wachberger, both of Basel, all of Switzerland

[73] Assignee: Hoffmann-La Roche Inc., Nutley, N.J.

[21] Appl. No.: 699,014

[22] Filed: Jun. 23, 1976

[30] Foreign Application Priority Data

Jul. 7, 1975 [CH] Switzerland ............... 8837/75

[51] Int. Cl.$^2$ .............................................. G01N 1/10
[52] U.S. Cl. ..................................... 222/1; 23/230 R; 23/259
[58] Field of Search ............. 222/14, 16, 17, 1, 144.5; 73/423 A; 23/259, 230 R; 417/477, 476

[56] References Cited

U.S. PATENT DOCUMENTS 4,002,269  1/1977  Negersmith ................. 23/259 X

Primary Examiner—Robert B. Reeves
Assistant Examiner—John P. Shannon

Attorney, Agent, or Firm—Samuel L. Welt; George M. Gould; Mark L. Hopkins

[57] ABSTRACT

Process and device for the automatic dilution of solutions using a peristaltic pump. Successive dilution processes can be carried out with a relative precision that remains high for a long time and without manual interference, with the advantage that the device is easily adjustable to any desired degrees of dilution. The peristaltic pump rotates continuously at a constant rate in one direction and the suction line immerses alternately, in each case during a certain number of pump strokes, in the solution to be diluted and in a diluent. A dilution operation is comprised of three stages, in which the suction tube is immersed in the diluent in the first and last stages and in the solutions to be diluted in the middle stage. The pump is comprised of a sensor for monitoring the temporal sequence of the contact of the pump cylinders with the feed tube in order to emit an appropriate output signal, a device for moving the suction line into the two immersion positions in separate locations, and a control unit for controlling the moving device synchronously with the sensor signals.

9 Claims, 1 Drawing Figure

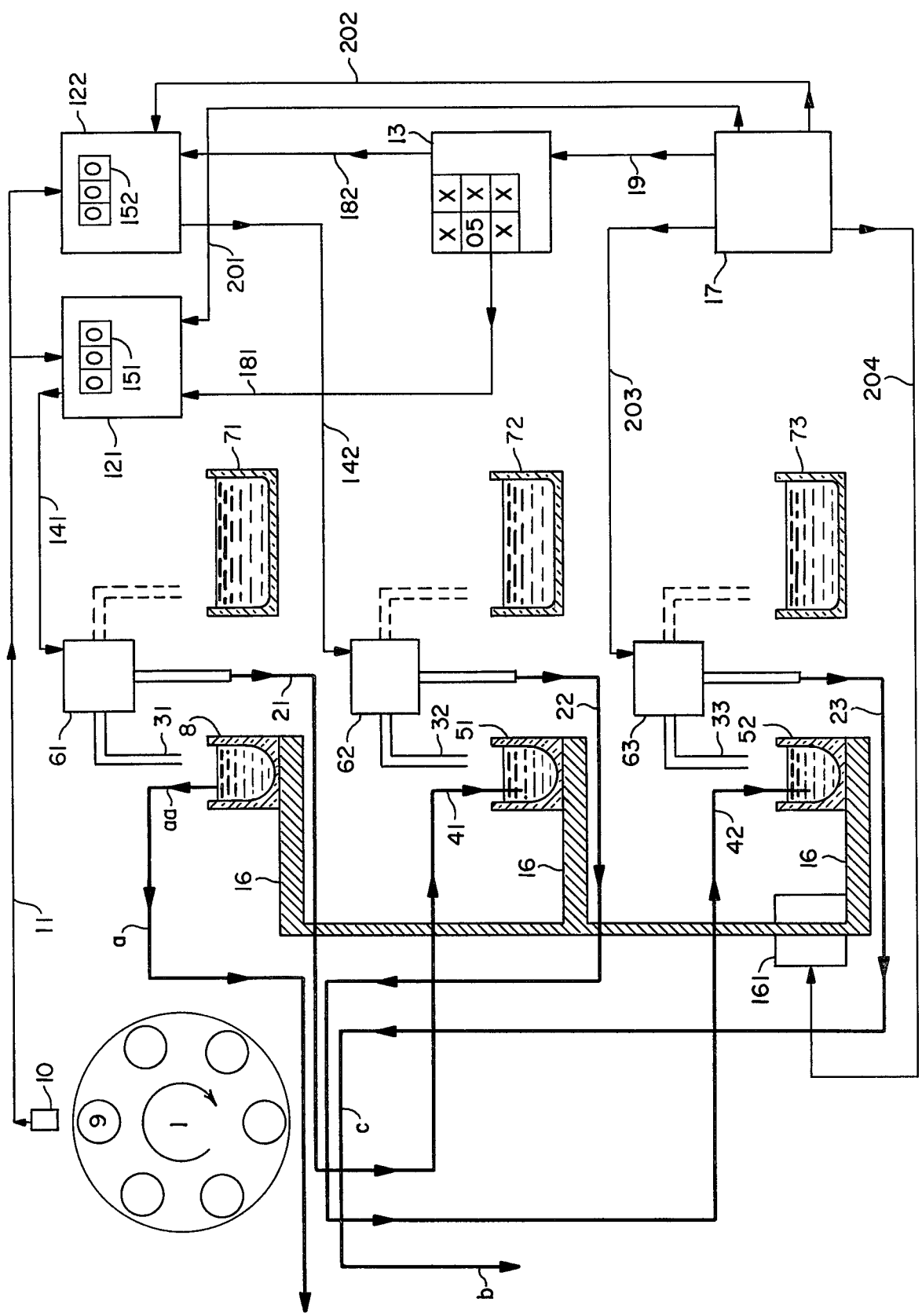

PROCESS AND DEVICE FOR THE AUTOMATIC DILUTION OF SOLUTIONS

BACKGROUND OF THE INVENTION

The invention relates to a process for the automatic dilution of solutions by means of a peristaltic pump and to a device for carrying out this process.

The dilution of a solution (also called concentrate in the following) to a certain smaller concentration is carried out by mixing this solution with a solvent in the appropriate ratio. This requires the setting up of an exact ratio between two volumes of liquid. If the two liquids are brought together by means of agents which serve to feed both the liquids to a mixing device it is necessary, in order to avoid incorrect dilutions, to clean or to rinse between two dilution operations the parts of the apparatus which come into contact with the media.

SUMMARY OF THE INVENTION

The object of the present invention consists in providing a device with which successive dilution processes can be carried out with a relative precision which is constantly high for a long time and without manual interference, the apparatus furthermore being easily adjustable to any desired degrees of dilution and allowing an easily understandable method of operation.

According to the invention this is achieved by a process of the type mentioned initially, which process is distinquished by the fact that the peristaltic pump rotates continuously at a constant rate in one direction and the suction line immerses alternately, in each case during a certain number of pump strokes, in the solution to be diluted and in a diluent.

With regard to a preferred embodiment of the process according to the invention, a dilution operation is comprised of three stages, the suction tube immersing in the diluent in the first and last stages and in the solution to be diluted in the middle stage.

The apparatus according to the invention comprises a peristaltic pump which rotates continuously at a constant rate in one direction and is distinguished by:
- a sensor which monitors the temporal sequence of the contact of the crushing cylinders with the feed tube and which emits an electrical impulse when a cylinder approaches;
- a device which moves the suction line into two immersion positions in separate locations; and
- a control unit which controls the movements of this device synchronously with the sensor impulses emitted from the sensor.

The underlying principle of the apparatus according to the invention for the exact setting-up of volume ratios consists in the following: The time slope of the rate of flow of the liquid conveyed by the peristaltic pump is periodic. The minimum of the rate of flow is virtually zero. The length of the period is equal to the reciprocal frequency of the crushing cylinders of the pump. It was shown that the amount of water conveyed between two contacts of the crushing cylinders:

$$\int_{t_1}^{t_2} V \cdot A \cdot dt = \delta Q \quad (1)$$

where
$V$: instantaneous rate of flow
$A$: diameter of tube
$(t_1 - t_2)$: length of period
is constant over a prolonged period of time (if the pump runs continuously) and only changes with the elasticity of the tubes.

If a sensor which produces an electrical impulse when the crushing cylinders pass through is fitted to the pump, the unit amount $\delta Q$ is then conveyed between two impulses of this type.

DESCRIPTION OF THE PREFERRED EMBODIMENT(s)

An embodiment of the subject of the invention is described in the following with the aid of the drawing which shows, in the form of a block diagram, an apparatus for the automatic dilution of a concentrate. It is an apparatus which dilutes a concentrate in two steps and which feeds the finished diluted solution to a subsequent apparatus, for example, an automatic analyzer. In the following the method of operation of the first dilution step is explained. The second step functions exactly as the first.

In this diagram 1 designates a peristaltic pump, which has a rotational speed which can be adjusted exactly and which runs continuously in one direction, which on the other hand leads to the suction nozzles 31 and 32 via the tube line sections 21 and 22 and on the other hand feeds the containers 51 and 52, for the dilute solutions, via the second tube line sections 41 and 42. Th container 51 receives the diluted solution of the first dilution step and subsequently serves as a reservoir for the second dilution step. The suction nozzles 31 and 32 can be swivelled, by means of the operating machinery 61 and 62, between the containers 8 and 51, with the concentrates, and the containers 71 and 72, which contain the diluent, and can be immersed in the inside of these containers. The peristaltic pump 1 has an approach sensor 10 which responds to the passing of the crushing cylinders 9 and which is connected to the control units 121 and 122 via the indicator lead 11. These controls units essentially contain a counting device which is controlled by the approach sensor 10 and the dilution ratios fed in from the memory 13 by the leads 181 and 182. This counting device actuates (not shown) a means of controlling the operating machinery 61 and 62, which are connected to the control units via the leads 141 and 142.

In order to be able to feed the desired dilution ratio in percentage proportions of the concentrate in the diluted solution directly into the memory 13 the counting arrangement is so constructed that with each dilution operation (in each step) a total of 100 units, corresponding to 100 approach impulses or 100 crushings of the piece of tube C, are counted. In addition, the arrangement counts an adjustable number of empty units which are necessary, in a manner described later, for emptying the suction feed section between the outlets of the suction nozzles 31 and 32 and the free end of the tube line sections 41 and 42.

The containers 8, 51 and 52 are located on the conveying apparatus 16 which ensures that successive samples are conveyed under the suction nozzles. The operating machinery 161 of the conveying apparatus receives the necessary sample change signals from the central dilution program control unit 17 via the control lead 204. The program control unit 17 superposed controls the dilution operation for all samples on the conveying apparatus via the control leads 19, 201 and 202, as well as the operating machinery 63 of the suction nozzle 33. The suction nozzle 33 conveys either the finished diluted sample from container 52 or rinsing agent from container 73 through the tube 23 into the subsequent analysis apparatus via the peristaltic pump 1. The control signals of the program control unit 17 are transferred to the operating machinery 63 via the lead 203. With the aid of the nozzle aa, the tube a and the peristaltic (sic) pump 1 the level of the liquid in the concentrate container 8 is sucked off to a constant height before the start of the dilution operation. The movement of the nozzle aa is effected via an (not shown) apparatus which is likewise controlled by the program control unit 17.

Because the suction nozzle 31 requires a certain time for the passage between its stationary position and reaching the level of the liquid, while on the other hand the pump continues to run continuously during this time, a small metering error arises during this immersion movement. This is already negligibly small in the case of amounts being conveyed by 2 to 3 pump strokes but could prove to be troublesome in the case of dilution ratios of 1:100. Because in this case the delay between immersion signal and penetration of the surface of the liquid is of about the same magnitude as the delay between the emersion signal and leaving the liquid, the nozzle is then in the liquid long enough if its passage from the stationary position to the surface of the liquid is about equally as long as the immersion depth. Thus, it is sufficient to ensure that the level of the liquid referred to, in the special case, of the concentrate, is maintained virtually constant so that a very accurate result can be achieved even in the case of extreme dilution ratios.

All the amounts of liquid of the entire dilution apparatus are conveyed through a large number of tubes via one and the same peristaltic pump.

When the apparatus is started up the peristaltic pump 1 is initially set in motion separately, the suction nozzles aa, 31 and 32 being emersed. The suction nozzle 33 on the other hand is immersed in the container 73 and conveys the rinsing agent to the analysis apparatus.

The program control unit 17 signals the conveying apparatus 161 and 16 to move the first container with concentrate under suction nozzles aa and 31. The nozzle aa is lowered and the level of the liquid of the concentrate is sucked off to a certain height. The information about the percentage proportion of concentrate for the first dilution step of the first sample is transmitted from the memory 13 to the counter 151 of the control unit 121 via the lead 181. The second dilution step (suction nozzle 32) and the sample feed (suction nozzle 33) are not active during this first dilution operation of the first sample. In the following description a dilution operation with a concentrate proportion in the finished solution of 5% is to be illustrated.

The number "05" in the memory 13 refers to this. The counter 151 in the control unit 121 stands at "000", in spite of the pump being in operation.

After the program control unit 17 has relayed the start signal via the lead 201, the subsequent impulse of the approach sensor 10 causes the suction nozzle 31 to immerse in the diluent container 71 and the counter 151 in the control unit 121 to start to count. Thus, a dilution cycle is started. Since in most dilution operations the concentrate proportion is considerably smaller than the diluent proportion, it is necessary in such cases to convey a smaller proportion of the amount of diluent at the start of the cycle so that the tube sections 21 and 22 are filled up to C with liquid and not with air. Equation (1) is only valid under this condition.

This proportion of diluent spans 10 pump cycles in the present example, corresponding to a count of 10 in the control unit.

As soon as this count is achieved the control unit 121 signals the operating machinery 61 to emerse the suction nozzle 31, synchronously with the sensor impulse, from the container 71 and the counting (sic) 151 is stopped. On the next impulse of the approach sensor 10 the control unit 121 signals the suction nozzle 31 to immerse in the container 8. The number of pump cycles corresponding to the contents of of the memory ("005") are now counted in the counter 151 until, in this example, the number "15" appears on the counter. Thus, after the 10 diluent strokes, a short inflow of air on changing the suction nozzle 31 from container 71 to container 8 and the 5 concentrate strokes 15 parts of liquid have now already been conveyed. During the 85 pump cycles remaining up to the count 100 the suction nozzle 31 and the tube line sections 21, C and 41 are rinsed free of residues of the concentrate. When the count of 100 is reached on the counter 151 the suction nozzle 31 is synchronously moved back to its emersed stationary position. The amount of diluent which is still in the tube line sections 21, C and 41 still belong, of course, to the last sample and must be forced out before a new dilution cycle begins. The pump 1, which continuously rotates further, now sucks in air at the opening of the suction nozzle 31. As soon as the counter 151 indicates a pump cycle number at which, according to experience, the tube line sections 21, C and 41 are empty, for example, when the count of 125 is achieved, the counter 151 is adjusted back to "000". The dilution cycle under consideration is complete.

Because the amount of liquid conveyed during a dilution cycle mostly also corresponds to a desired sample amount or emptying amount, an identical empty container, in place of the container 51 which was filled before, must be brought under the free end of the tube line section 41 before or immediately after the start of a new cycle. This is effected by the conveying apparatus 161 and 16 on a signal from the program control unit 17 as soon as the end of the dilution operation of the first step is announced via the lead 201.

At this point in time the suction nozzle 31 is again in its starting position above the container 71 containing dilution liquid; the peristaltic pump 1 continuously rotates further. When the next impulse of the approach sensor 10 occurs, the entire operation for the first dilution step is repeated (with, however, a new number from the memory 13 corresponding to the sample number 2). However, the second dilution step now also begins simultaneously to operate exactly analogously to the first, since the container 51 is now filled. It is obvious that the outflow nozzles 41 and 42 must each be displaced by one sample position on the conveying apparatus with respect to the position of the suction nozzles 32 and 33 since the two dilution operations for the same sample must be effected one after the other. This means: if sample number N is in the first dilution step, the sample (N−1), which has already undergone one dilution step, is in the second dilution step and the sample (N−2), which has undergone two dilution steps (finished [sample]) is in the reservoir ready for the analysis apparatus. After the last sample has been diluted by the first step, the operating sequence is effected accordingly: in the next position of the conveying apparatus the second dilution step and the suction nozzle 33 are still active, and in the next but one and last position to (sic) the conveying apparatus only the suction nozzle 33 is still active. The program control unit 17 ensures the correct course of this sequence.

For the purpose of a simplified representation the invention has been shown on an apparatus in which the dilution liquid, which is proportionately predominate, was metered in two stages and the concentrate, on the other hand, was metered in a single feed stage. It is obvious that the delivery of the concentrate could, of course, also be effected in several stages. The choice of the successive feed stages is in itself limited only by the development standard of the control unit and could thus be adjusted to suit any desired demands.

In the apparatus described for the automatic dilution of solutions it is of substantial importance that the solution and the dilution liquid are not pumped through two different tube lines but through the same tube line, it being possible to subsequently rinse the tube line with plenty of dilution liquid after the metering of the solution has been effected. Likewise, the fact that concentrate and diluent are always conveyed in the same direction and that the peristaltic pump runs continuously is of fundamental importance. This has the advantage that the formation of drops on the outflow nozzles 41 and 42 scarcely impair the accuracy since the amount of concentrate, which is normally small, is conveyed through outflow nozzles which have been wetted or rinsed with diluent. A premature mixing (insufficient washing out of the concentrate) of concentrate and solvent is prevented by the intermediate flow of air. Furthermore, if transparent tube lines are used it can be easily visually checked at all times whether the apparatus is functioning in an orderly manner.

The rollers of the pump, which run over the feed tube, effect a pulsating movement of the liquid column in the tube line, a certain amount of liquid, which remains virtually constant, being conveyed in each case. By using a single feed tube the long term alteration of the absolute feed capacity occurring as a result of ageing is insignificant because it applies in each case to both mixing components to the same degree.

The phase relationship of the electrical impulse produced by the approach of the crushing cylinders 9 to the sensor 10 is adjusted so that the impulse is always given out when the thread of liquid in the tubes is stationary. Therefore, the immersion and emersion of the suction nozzles 31 and 32, which is controlled by the sensor impulse, is effected virtually when the thread of liquid is stationary. The effective dilution ratio is therefore given with high accuracy from the ratio of the number of impulses counted during the immersion of the suction nozzle in the concentrate to the number of impulses counted during the immersion of the suction nozzle in the diluent.

The dilution process described above, compared with similar existing processes, has the advantage that by means of this process any desired number of liquid samples can be diluted automatically, and with a high relative accuracy, to any desired ratios which change from sample to sample.

The accuracy and reproducibility of the dilution ratios can be represented by simple statistical relationships and are based on the present measurement results:

The earlier description concerning the importance of conveying a smaller proportion of the diluent at the start of the cycle is of particular importance for the correctness of the particular dilution, particularly in the case of extreme dilution ratios (1 + 99). By exactly adjusting the suction nozzle $aa$ with an appropriate gauge an absolute deviation of $\pm 0.3\%$ is achieved even under the extreme ratios. For smaller dilution ratios (from 3 + 97) this tends towards zero.

The variation coefficient of one-step dilution (1 + 99) is $\pm 0.5\%$. The law of error propagation, that is to say the root of the sum of the variances, applies to the multi-step [dilution].

For smaller dilution ratios (2 + 98, 3 + 97 and the like), the variation coefficient decreases with the factor $1/\sqrt{\text{roll number}}$, that is to say $1/\sqrt{2}$ $1/\sqrt{3}$ and the like.

Thus, the correctness and the reproducibility for any desired dilution ratios can be calculated using these numerical data.

The use of the dilution principle described was shown in the example of an automatic two-step dilution apparatus. However, the apparatus could without doubt be extended to further steps.

A further use of the principle consists in the simultaneous dilution of groups of samples, the individual samples of which are to be diluted in the same ratios. In addition, as many suction nozzles as corresponds to the number of the samples of a group are moved parallel by a single control unit.

Generally the principle can be used to convey, transfer and meter liquids (solvents, reagents and the like).

What is claimed is:

1. Process for the automatic dilution of concentrated solutions with a diluent by means of a peristaltic pump comprising having a peristaltic pump run continuously at a constate rate in one direction thereby defining a suction end and a dispensing end of the pump and for each diluting cycle immersing the suction end alternatively, for a certain number of pump strokes, in the concentrated solution and in the diluent, wherein a dilution operation is comprised of three stages, in which the suction line is immersed in the diluent in the first and last stages and in the solution to be diluted in the middle stage.

2. Process according to claim 1 wherein the sum of the pump strokes in the three stages of dilution operation is a constant number.

3. Process according to claim 2 wherein the constant number is 100 and the number of the pump strokes of the middle stage accordingly directly indicates the dilution ratio.

4. Device for the automatic dilution of concentrated solutions with a diluent, having a peristaltic pump which runs continuously at a constant rate in one direction, thereby defining a suction end and a dispensing end of the pump, and which has crushing cylinders and a feed tube, comprising:
    (a) first means for monitoring the time sequence of the contact of the crushing cylinders with the feed tube and for emitting an electrical impulse when a cylinder approaches;
    (b) second means for moving a suction line associated with the pump into two immersion positions in separate locations; and
    (c) a control unit for controlling the movements of said second means synchronously with the impulses of said first means, said control unit including third means for counting the impulses emitted from said first means.

5. Device according to claim 4 further including means connected to the control unit for preselecting the desired dilution ratios.

6. Device according to claim 5 wherein at least one other substantially identical device is subsequently connected for the further dilution of the already diluted solution.

7. Device according to claim 5 further including a memory unit for storing the pre-selected dilution ratios.

8. Device according to claim 6 further including containers containing the concentrated solution and containers for collecting the solutions diluted in the initial dilution, wherein said latter-mentioned containers are arranged on a conveying device on which there are also the containers containing the concentrated solution.

9. Device according to claim 8 further including means for maintaining a constant liquid level in the containers containing the concentrated solution and the diluent.

* * * * *